United States Patent
Wiles et al.

(10) Patent No.: US 10,458,887 B2
(45) Date of Patent: Oct. 29, 2019

(54) METHOD OF SAMPLE PREPARATION FOR MALDI AND AUTOMATED SYSTEM THEREFOR

(71) Applicant: Becton, Dickinson and Company, Franklin Lakes, NJ (US)

(72) Inventors: Timothy Wiles, Manchester, MD (US); John D. Mantlo, Westminster, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/504,549

(22) PCT Filed: Aug. 17, 2015

(86) PCT No.: PCT/US2015/045506
§ 371 (c)(1),
(2) Date: Feb. 16, 2017

(87) PCT Pub. No.: WO2016/028684
PCT Pub. Date: Feb. 25, 2016

(65) Prior Publication Data
US 2017/0234780 A1    Aug. 17, 2017

Related U.S. Application Data

(60) Provisional application No. 62/038,509, filed on Aug. 18, 2014.

(51) Int. Cl.
*G01N 1/38* (2006.01)
*G01N 1/28* (2006.01)
(Continued)

(52) U.S. Cl.
CPC ............ *G01N 1/38* (2013.01); *G01N 1/2813* (2013.01); *G01N 1/4022* (2013.01); *G01N 1/44* (2013.01);
(Continued)

(58) Field of Classification Search
None
See application file for complete search history.

(56) References Cited

U.S. PATENT DOCUMENTS

2004/0119010 A1    6/2004   Perryman et al.
2005/0275837 A1   12/2005   Zhang et al.
(Continued)

FOREIGN PATENT DOCUMENTS

CN    102749233 A    10/2012
JP    2004101408 A    4/2004
(Continued)

OTHER PUBLICATIONS

Keller, B.O. et al., Three-Layer Matrix/Sample Preparation Method for MALDI MS Analysis of Low Nanomolar Protein Samples, 2006, J. Am. Soc. Mass Spectrom. vol. 17, pp. 780-785.*
(Continued)

*Primary Examiner* — Xiaoyun R Xu
(74) *Attorney, Agent, or Firm* — Botos Churchill IP Law LLP

(57) ABSTRACT

Methods for preparing a biological sample for testing by Maldi where such methods are selected based on sample parameters. Maldi scores are obtained for a range of sample parameters (e.g. McFarland, dispense volume and number of dispenses). From the data, sample preparation parameters can be selected for a biological sample being prepared for Maldi testing. One sample preparation strategy uses multiple dispenses of sample with an intervening drying step, which
(Continued)

yields more accurate Maldi scores, particularly for samples at the low range of McFarland values (e.g. below about 2).

9 Claims, 14 Drawing Sheets

(51) Int. Cl.
| | |
|---|---|
| *G01N 1/44* | (2006.01) |
| *G01N 35/00* | (2006.01) |
| *G01N 35/10* | (2006.01) |
| *G01N 1/40* | (2006.01) |
| *H01J 49/04* | (2006.01) |
| *H01J 49/40* | (2006.01) |
| *G01N 15/06* | (2006.01) |

(52) U.S. Cl.
CPC ... *G01N 35/00722* (2013.01); *G01N 35/1016* (2013.01); *G01N 2001/4027* (2013.01); *G01N 2015/0693* (2013.01); *H01J 49/0413* (2013.01); *H01J 49/0418* (2013.01); *H01J 49/0468* (2013.01); *H01J 49/40* (2013.01)

(56) References Cited

U.S. PATENT DOCUMENTS

| | | |
|---|---|---|
| 2006/0032071 A1 | 2/2006 | Baba et al. |
| 2008/0067345 A1 | 3/2008 | Fenn |
| 2010/0038529 A1 | 2/2010 | Sato et al. |
| 2010/0120085 A1 | 5/2010 | Hyman et al. |
| 2012/0009558 A1 | 1/2012 | Armstrong et al. |
| 2012/0070902 A1 | 3/2012 | Shimaoka et al. |
| 2013/0022962 A1* | 1/2013 | Galiano ............... C12M 41/36 435/5 |
| 2013/0320203 A1 | 12/2013 | Roder et al. |

FOREIGN PATENT DOCUMENTS

| | | |
|---|---|---|
| JP | 2006504971 A | 2/2006 |
| JP | 2012073197 A | 4/2012 |
| WO | 2004042072 A2 | 5/2004 |
| WO | 2004051234 A1 | 6/2004 |
| WO | 2004092703 A2 | 10/2004 |
| WO | 2009065580 A1 | 5/2009 |
| WO | 2013147610 A2 | 10/2013 |
| WO | 20130147610 A2 | 10/2013 |

OTHER PUBLICATIONS

Liu, H. et al. Universal Sample Preparation Method for Characterization of Bacteria by Matrix-Assisted Laser Desorption Ionization—Time of Flight Mass Spectrometry, 2007, Applied and Environmental Microbiology, vol. 73(6), pp. 899-1907 (Year: 2007).*

International Search Report for Application No. PCT/US2015/045506 dated Oct. 29, 2015.

Schmidt, et al., "Rapid identification of bacteria in positive blood culture by matrix-assisted laser desorption ionization time-of-flight mass spectrometry", Eur J Clin Microbiol Infect Dis, Jun. 23, 2011, pp. 1-7, DOI 10.1007/s10096-011-1312-0, Springer-Verlag, Germany.

Herendael, et al., "Validation of a modified algorithm for the identification of yeast isolates using matrix-assisted laser desorption/ionisation time-of-flight mass spectrometry (MALDI-TOF MS)", Eur J Clin Microbiol Infect Dis, Aug. 23, 2011, pp. 1-8, DOI 10.1007/s10096-011-1383-y, Springer-Verlag, Germany.

Bizzini, et al., "Improved Performance for Bacteria and Yeast Identification by a commercial Matrix-Assisted Laser Desoprtion Ionisation-Time-of Flightf Mass Spectrometry (MALDI-TOF) system in the Clinical Microbiology Laboratory", J.Clin. Microbiol., doi: 10.1128/JCM.00576-11, Jul. 6, 2011, 48: 1549-1554.

Miliotis T et al: Ready-made matrix-assisted laser desorption/ionization target plates coated within thin matrix layer for automated sample deposition in high-density array format: Rapid Communications in Mass Spectrometry, John Wiley & Songs, GB, No. 16, Jan. 1, 2002, pp. 117-126 Xp002959100, ISSN: 0951-4198, DOI: 10.102/RCM.542; p. 123, right column.

Kern Carola C et al "Optimization of Matrix-Assisted-Laser-Desorption-Ionization-Time-of-Flight Mass Spectrometry for the identification of bacterial contaminants in bever" Journal of Microbiological Methods, Elsevier, Amsterdam, NL, vol. 93, No. 3, Mar. 26, 2013, pp. 185-191, XP028534145, ISSN: 0167-7012, DOI: 10.1016/J.MIMET.2013.03.012 * abstract* * table 3* * p. 186, right col. 2.2 sample preparation*.

Simon Ekstrom et al "Signal Amplification Using "Spot-on-a-Chip" Technology for the Identification of Proteins via MALDI-TOF MS", Analytical Chemistry, vol. 73, No. 2, Sep. 12, 2000, pp. 214-219, XP055459597, ISSN: 0003-2700, DOI: 10.1021/ac000734u *abstract*.

Supplementary EP Search Report Received in European Application No. 15833985.3 , dated Mar. 26, 2018, pp. 9.

Japanese Office Action received in JP2017-508981 dated May 21, 2019.

CN Office Action received in 2015800498503 dated Apr. 2, 2019, pp. 24.

\* cited by examiner

FIG. 1

Table 400:

| Run# | Volume | Dispenses | McFarland |
|---|---|---|---|
| 1 | 0.5 | 1 | 0.25 |
| 6 | 1 | 2 | 0.25 |
| 11 | 2 | 3 | 0.25 |
| 16 | 4 | 4 | 0.25 |
| 2 | 0.5 | 2 | 0.5 |
| 5 | 1 | 1 | 0.5 |
| 12 | 2 | 4 | 0.5 |
| 15 | 4 | 3 | 0.5 |
| 3 | 0.5 | 3 | 1.0 |
| 8 | 1 | 4 | 1.0 |
| 9 | 2 | 1 | 1.0 |
| 14 | 4 | 2 | 1.0 |
| 4 | 0.5 | 4 | 2.0 |
| 7 | 1 | 3 | 2.0 |
| 10 | 2 | 2 | 2.0 |
| 13 | 4 | 1 | 2.0 |

*Additional conditions added on 4/10/2014

Table 500:

| Run# | Volume | Dispenses | McFarland |
|---|---|---|---|
| 17 | 0.5 | 1 | 5.0 |
| 18 | 4 | 4 | 5.0 |
| 19 | 4 | 1 | 5.0 |
| 20 | 1 | 4 | 5.0 |
| 21 | 1 | 3 | 5.0 |
| 22 | 2 | 1 | 5.0 |

NOTE: PhoenixSpec Nephelometer only accurate to 4.0, to create a 5.0 McFarland the suspension was diluted 1:2 in BBL sterile water
→ 5.0 McFarland diluted 1:2 = 2.0
→ 6.0 McFarland diluted 1:2 = 2.5
For this experiment a 6.0 McFarland value was created for each test organism.

FIG. 2

| Organism | Strain |
|---|---|
| Bacillus cereus | 1059 |
| Corynebacterium jeikeium | 1086 |
| Enterococcus faecalis | C2038 |
| Listeria monocytogenes | 23 |
| Staphylococcus aureus | 313 |
| Staphylococcus epidermidis | 274 |
| Staphylococcus haemolyticus | 489 |
| Streptococcus pneumoniae (mucoid) | 650 |
| Streptococcus pneumoniae | 3093 |
| Streptococcus pyogenes (Strep. group A) | 2979 |
| Streptococcus gallolyticus | 1208 |
| Achromobacter xylosoxidans ssp xylosoxidans | 10431 |
| Pseudomonas fluorescens | 8832 |
| Alcaligenes faecalis | 9139 |
| Citrobacter freundii | 9905 |
| Citrobacter koseri | 9190 |
| Enterobacter aerogenes | 10148 |
| Enterobacter cloacae | 7988 |
| Escherichia coli | 10234 |
| Klebsiella oxytoca | 8025 |
| Klebsiella pneumoniae ssp pneumoniae (mucoid) | 14778 |
| Klebsiella pneumoniae ssp pneumoniae | 9605 |
| Proteus mirabilis | 10070 |
| Proteus vulgaris | 13027 |
| Stenotrophomonas maltophilia | 9895 |
| Escherichia coli | A25922 |
| Staphylococcus aureus | A29213 |
| Enterococcus faecalis | A29212 |
| Pseudomonas aeruginosa | A27853 |

FIG. 3A

| Organism | |
|---|---|
| Bacillus cereus | 1059 |
| Corynebacterium jeikeium | 1086 |
| Enterococcus faecalis | C2038 |
| Staphylococcus aureus | 313 |
| Staphylococcus epidermidis | 274 |
| Staphylococcus haemolyticus | 489 |
| Streptococcus pneumoniae (mucoid) | 650 |
| Streptococcus pneumoniae | 3063 |
| Streptococcus gallolyticus | 1268 |
| Pseudomonas fluorescens | 8632 |
| Citrobacter freundii | 9905 |
| Enterobacter cloacae | 7988 |
| Escherichia coli | 10234 |
| Klebsiella pneumoniae ssp pneumoniae (mucoid) | 14778 |
| Stenotrophomonas maltophilia | 9595 |

FIG. 3B

| Run# | Volume | Dispenses | McFarland | % Correct |
|---|---|---|---|---|
| 1 | 0.5 | 1 | 0.25 | 2% |
| 2 | 0.5 | 2 | 0.5 | 22% |
| 3 | 0.5 | 3 | 1.0 | 63% |
| 4 | 0.5 | 4 | 2.0 | 78% |
| 5 | 1 | 1 | 0.5 | 18% |
| 6 | 1 | 2 | 0.25 | 35% |
| 7 | 1 | 3 | 2.0 | 91% |
| 8 | 1 | 4 | 1.0 | 91% |
| 9 | 2 | 1 | 1.0 | 78% |
| 10 | 2 | 2 | 2.0 | 96% |
| 11 | 2 | 3 | 0.25 | 78% |
| 12 | 2 | 4 | 0.5 | 80% |
| 13 | 4 | 1 | 2.0 | 100% |
| 14 | 4 | 2 | 1.0 | 96% |
| 15 | 4 | 3 | 0.5 | 78% |
| 16 | 4 | 4 | 0.25 | 84% |
| 17 | 0.5 | 1 | 5.0 | 62% |
| 18 | 4 | 4 | 5.0 | 89% |
| 19 | 4 | 1 | 5.0 | 100% |
| 20 | 1 | 4 | 5.0 | 100% |
| 21 | 1 | 3 | 5.0 | 96% |
| 22 | 2 | 1 | 5.0 | 96% |

FIG. 5

| Organism | 0.25 McF 1ul/1ul (Complete Drying Between Sample Additions) | | 0.25 McF 1ul/1ul (Incomplete Drying Between Sample Additions) | |
|---|---|---|---|---|
| Bacillus cereus 1059 | Bacillus cereus | 1.869 | Bacillus cereus | 2.036 |
| | Bacillus cereus | 2.117 | Bacillus cereus | 1.961 |
| | Bacillus cereus | 2.035 | Bacillus cereus | 1.947 |
| Corynebacterium jeikeium 1086 | not reliable identification | 1.404 | not reliable identification | 1.12 |
| | not reliable identification | 1.484 | not reliable identification | 1.293 |
| | not reliable identification | 1.429 | not reliable identification | 1.43 |
| Enterococcus faecalis C2038 | Enterococcus faecalis | 2.196 | Enterococcus faecalis | 2.035 |
| | Enterococcus faecalis | 2.011 | Enterococcus faecalis | 2.12 |
| | Enterococcus faecalis | 2.152 | Enterococcus faecalis | 2.161 |
| Staphylococcus aureus 313 | Staphylococcus aureus | 2.03 | Staphylococcus aureus | 2.202 |
| | Staphylococcus aureus | 2.144 | Staphylococcus aureus | 2.186 |
| | Staphylococcus aureus | 2.3 | Staphylococcus aureus | 1.961 |
| Staphylococcus epidermidis 274 | Staphylococcus epidermidis | 2.168 | Staphylococcus epidermidis | 2.119 |
| | Staphylococcus epidermidis | 2.08 | Staphylococcus epidermidis | 1.805 |
| | Staphylococcus epidermidis | 2.05 | Staphylococcus epidermidis | 1.93 |
| Staphylococcus haemolyticus 489 | Staphylococcus haemolyticus | 1.915 | not reliable identification | 1.583 |
| | Staphylococcus haemolyticus | 1.863 | Staphylococcus haemolyticus | 1.865 |
| | Staphylococcus haemolyticus | 2.068 | Staphylococcus haemolyticus | 2.104 |
| Streptococcus pneumoniae (mucoid) 650 | Streptococcus pneumoniae | 1.941 | Streptococcus pneumoniae | 2.106 |
| | Streptococcus pneumoniae | 1.959 | Streptococcus pneumoniae | 1.908 |
| | Streptococcus pneumoniae | 2.183 | Streptococcus pneumoniae | 1.871 |
| Streptococcus pneumoniae 3093 | Streptococcus pneumoniae | 2.034 | Streptococcus pneumoniae | 1.952 |
| | Streptococcus pneumoniae | 2.134 | Streptococcus pneumoniae | 1.827 |
| | Streptococcus pneumoniae | 2.002 | Streptococcus pneumoniae | 1.919 |

FIG. 6A

| Organism | 0.25 McF 1ul/1ul (Complete Drying Between Sample Additions) | | 0.25 McF 1ul/1ul (Incomplete Drying Between Sample Additions) | |
|---|---|---|---|---|
| Streptococcus gallolyticus 1268 | not reliable identification | | not reliable identification | |
| | not reliable identification | 1.28 | not reliable identification | 1.802 |
| | not reliable identification | 1.4 | Streptococcus gallolyticus | 1.733 |
| Pseudomonas fluorescens 8832 | Pseudomonas fluorescens | 2.105 | Pseudomonas fluorescens | 2.183 |
| | Pseudomonas libanensis | 2.019 | Pseudomonas libanensis | 2.064 |
| | Pseudomonas fluorescens | 2.045 | Pseudomonas fluorescens | 2.104 |
| Citrobacter freundii 9935 | Citrobacter freundii | 2.253 | Citrobacter freundii | 2.071 |
| | Citrobacter freundii | 2.217 | Citrobacter freundii | 2.235 |
| | Citrobacter freundii | 2.131 | Citrobacter freundii | 2.241 |
| Enterobacter cloacae 7988 | Enterobacter cloacae | 2.075 | Enterobacter cloacae | 2.159 |
| | Enterobacter cloacae | 1.932 | Enterobacter cloacae | 2.103 |
| | Enterobacter cloacae | 2.084 | Enterobacter cloacae | 2.245 |
| Escherichia coli 10234 | Escherichia coli | 2.007 | Escherichia coli | 2.045 |
| | Escherichia coli | 1.996 | Escherichia coli | 2.039 |
| | Escherichia coli | 1.989 | Escherichia coli | 2.061 |
| Klebsiella pneumoniae ssp pneumoniae (mucoid) 14778 | Klebsiella pneumoniae | 2.194 | Klebsiella pneumoniae | 2.08 |
| | Klebsiella pneumoniae | 2.151 | Klebsiella pneumoniae | 1.9 |
| | Klebsiella pneumoniae | 2.077 | Klebsiella pneumoniae | 2.063 |
| BTS (E. coli - Bacterial Test Standard) | Escherichia coli | 2.33 | Escherichia coli | 2.294 |
| | Escherichia coli | 2.11 | Escherichia coli | 2.322 |

| Organism | 0.25 McF 1ul | | 0.25 McF 2ul | | 0.25 McF 1ul/1ul | |
|---|---|---|---|---|---|---|
| Streptococcus pneumoniae (mucoid) 820 | Streptococcus pneumoniae | 1.909 | Streptococcus pneumoniae | 1.905 | Streptococcus pneumoniae | 2.06 |
| | Streptococcus pneumoniae | 1.873 | Streptococcus pneumoniae | 1.948 | Streptococcus pneumoniae | 2.172 |
| | not reliable identification | 1.651 | not reliable identification | 1.659 | Streptococcus pneumoniae | 1.979 |
| Streptococcus pneumoniae 3043 | Streptococcus pneumoniae | 1.965 | Streptococcus pneumoniae | 1.868 | Streptococcus pneumoniae | 2.142 |
| | Streptococcus pneumoniae | 1.72 | Streptococcus pneumoniae | 1.99 | Streptococcus pneumoniae | 1.964 |
| | not reliable identification | 1.651 | Streptococcus pneumoniae | 2.003 | Streptococcus pneumoniae | 2.02 |
| Streptococcus gallolyticus 1268 | not reliable identification | 1.59 | not reliable identification | 1.531 | not reliable identification | 1.534 |
| | not reliable identification | 1.588 | not reliable identification | 1.66 | not reliable identification | 1.93 |
| | not reliable identification | 1.686 | not reliable identification | 1.579 | not reliable identification | 1.449 |
| Pseudomonas fluorescens 8632 | Pseudomonas libanensis | 2 | Pseudomonas fluorescens | 2.109 | Pseudomonas fluorescens | 2.073 |
| | Pseudomonas libanensis | 1.994 | Pseudomonas fluorescens | 1.99 | Pseudomonas rhodesiae | 2.003 |
| | Pseudomonas libanensis | 1.941 | Pseudomonas rhodesiae | 2.07 | Pseudomonas fluorescens | 2.051 |
| Citrobacter freundii 9305 | Citrobacter freundii | 2.166 | Citrobacter freundii | 2.375 | Citrobacter freundii | 2.227 |
| | Citrobacter freundii | 1.939 | Citrobacter freundii | 2.374 | Citrobacter freundii | 2.267 |
| | Citrobacter freundii | 2.170 | Citrobacter freundii | 2.202 | Citrobacter freundii | 2.399 |
| Enterobacter cloacae 7980 | Enterobacter cloacae | 2.19 | Enterobacter cloacae | 2.246 | Enterobacter cloacae | 2.157 |
| | Enterobacter cloacae | 2.078 | Enterobacter cloacae | 1.945 | Enterobacter cloacae | 2.071 |
| | Enterobacter cloacae | 1.922 | Enterobacter cloacae | 2.096 | Enterobacter cloacae | 2.249 |

FIG. 7B

| Organism | 0.25 McF 1ul | | 0.25 McF 2ul | | 0.25 McF 1ul/1ul | |
|---|---|---|---|---|---|---|
| Escherichia coli 10234 | Escherichia coli | 2.189 | Escherichia coli | 2.359 | Escherichia coli | 2.219 |
| | Escherichia coli | 1.903 | Escherichia coli | 2.319 | Escherichia coli | 2.086 |
| | Escherichia coli | 1.996 | Escherichia coli | 2.24 | Escherichia coli | 2.209 |
| Klebsiella pneumoniae ssp pneumoniae (mucoid) 14778 | Klebsiella pneumoniae | 2.135 | Klebsiella pneumoniae | 1.754 | Klebsiella pneumoniae | 2.299 |
| | Klebsiella pneumoniae | 2.147 | Klebsiella pneumoniae | 2.157 | Klebsiella pneumoniae | 2.15 |
| | Klebsiella pneumoniae | 2.153 | Klebsiella pneumoniae | 2.241 | Klebsiella pneumoniae | 2.205 |
| BTS (E. coli - Bacterial Test Standard) | Escherichia coli | 2.271 | Escherichia coli | 2.215 | Escherichia coli | 2.259 |

FIG. 7C

METHOD OF SAMPLE PREPARATION FOR MALDI AND AUTOMATED SYSTEM THEREFOR

CROSS-REFERENCE TO RELATED APPLICATIONS

The present application is a national phase entry under 35 U.S.C. § 371 of International Application No. PCT/US2015/045506 filed Aug. 17, 2015, published in English, which claims the benefit of the filing date of U.S. Provisional Application No. 62/038,509, filed Aug. 18, 2014, all of which are incorporated herein by reference.

BACKGROUND OF THE INVENTION

As a routine practice in medical diagnosis and treatment, biological samples such a blood or urine are obtained from a patient and analyzed for the presence of microorganisms. If microorganisms are determined to be present, there is both medical and economic justification to both identify the specific microorganism present and, to facilitate treatment, the antibiotic resistance/susceptibility of the microorganism. Often such determinations must be made quickly to ensure that the correct treatment is initiated as quickly as possible.

For example, sepsis is a serious medical condition caused by an overwhelming response of the host immune system to infection. It can trigger widespread inflammation, which can give rise to impaired blood flow. As sepsis progresses, the body's organs can be starved for oxygen and nutrients, causing permanent damage and eventual failure. Left improperly diagnosed or otherwise untreated, the heart weakens and septic shock can occur, leading to multiple organ failure and death. Blood cultures are required to detect the presence of bacteria or yeast in the blood of sepsis patients, to identify the microorganism(s) present and guide treatment. The conventional separation and identification of microorganism(s) from blood cultures takes at least 24-48 hours, which results in many of the septicemia patients being initially treated with inappropriate antibiotics. It is therefore desirable to separate and identify microorganisms from a positive culture (blood, cerebrospinal fluid etc.) rapidly.

Recently, certain proteomic technologies/tools, such as Matrix-Assisted Laser Desorption Ionization Time of Flight mass spectrometry, ("MALDI-TOF MS") ("Maldi" hereinafter), have been shown to provide a rapid and accurate identification of bacteria and/or fungi from a positive blood culture ("PBC") or from a bacterial colony grown on a substrate such as an agar plate.

In the Maldi process, small quantities of microbes from a colony cultivated in the usual way in a nutrient medium are transferred to a mass spectrometric sample support plate known as a Maldi plate, and then subjected directly to mass spectrometric analysis, generally by time-of-flight (TOF). The mass spectrum analysis shows the different proteins, provided they are present in the microbes in sufficient concentration. The identity of the microbe is then determined from the microbe's protein profile through a computerized search of spectral libraries containing thousands of reference spectra. If no reference mass spectrum is present in a library for the precise species of microbe being examined, computerized library searches with looser similarity requirements can provide at least some indication of the order, family or genus of the microbes, since related microbes frequently contain a number of identical protein types. The Maldi process is described in further detail in International Publication No. WO-2009/065580A1 to Ulrich Weller entitled "Identification of Pathogens in Bodily Fluids," the content of which is hereby incorporated in its entirety. A variety of mass spectrometry instruments may be used for identification.

The microorganism in the PBC sample can be subcultured prior to Maldi identification, e.g. on an agar plate. In the alternative, microorganisms can be isolated from the PBC sample using various sample preparation methods without the need for subculturing. The microorganism isolates are generally directly smeared onto a Maldi plate to yield about 70-80% identification accuracy. For isolates failing to yield any identification, a follow-up liquid extraction method is typically used to extract proteins from the microorganism for improved identification by MALDI-TOF MS. Although these liquid protein extraction methods generally yield better identification accuracy, such methods not only require several centrifugation steps, but also are time-consuming.

Schmidt, V. et al. "Rapid identification of bacteria in positive blood culture by matrix-assisted laser desorption ionization time-of-flight mass spectrometry," *Eur. J. Clin. Microbiol. Infect Dis*. Vol. 31(3), pp. 311-317 (March 2012) (Epub dated Jun. 23, 2011) discloses a method of identifying bacteria from positive blood cultures by spotting a liquid sample of the isolated bacteria onto a Maldi plate and overlaying 25% formic acid directly to the spotted liquid sample. Therefore, the final concentration of formic acid in the bacterial sample is less than 25%. The Schmidt method results in 86.6% identification accuracy for gram-negative bacteria and 60% identification accuracy for gram-positive bacteria. Schmidt did report testing this method in Yeast.

Hyman, J. et al. (U.S. Patent Publication No. 2010/0120085, Published May 13, 2010), discloses a similar method as Schmidt, in which intact isolated microorganisms in solution are directly smeared onto a Maldi plate. The liquid sample is then overlaid with roughly an equal volume of 50% formic acid. Therefore, the final concentration of formic acid added to the sample is approximately 25%. This method was tested on 14 different species of bacteria and yeast. Although this method resulted in 91.1% identification, the data does not indicate how effective this method is with regard to gram-positive bacteria, gram-negative bacteria, or yeast.

Haigh et al. "Improved Performance of Bacterium and Yeast Identification by a Commercial Matrix-Assisted Laser Desorption Ionisation-Time of Flight Mass Spectrometry System in the Clinical Microbiology Laboratory," *J. Clin. Microbiol*. Vol 49(9) p. 3441 (September 2011) describes a method in which neat formic acid is used to extract microbial proteins smeared directly onto a Maldi plate. This method, however, was unable to successfully identify all strains of yeast and gram-positive bacteria.

Herendael et al. "Validation of a modified algorithm for the identification of yeast isolates using matrix-assisted laser desorption/ionisation time-of-flight mass spectrometry (MALDI-TOF MS)", *Eur. J. Clin. Microbial. Infect Dis* Vol 31(5), pp. 841-848 (May 2012) (Epub Aug. 23, 2011) describes two methods for the identification of yeast. The standard extraction method described in Herendael et al., is a conventional liquid extraction method. In the short extraction method described in Herendael et al., one colony was picked from an agar plate and applied directly to the target Maldi plate. Formic acid (1 µL at 70% concentration) was added to the sample and the sample was allowed to dry. The dried sample was overlaid with Maldi matrix, allowed to dry further, and analyzed by MALDI-MS. The short extraction method provided identical results as the standard extraction method although the Maldi scores were lower with the short extraction method. Nearly all of the isolates (97.6%) could be identified with the short extraction method; however 17.1% of these identifications fell below the reliable threshold level of 1.7.

While the extraction method provides accurate results, time to detection (TTD) is much less than detection by direct smear. Therefore, methods that improve the accuracy of identification using direct smear Maldi are sought.

BRIEF SUMMARY OF THE INVENTION

Various embodiments of the disclosed method enable direct identification of microorganisms from positive blood cultures ("PBC") or pure isolates of bacterial colonies cultured on a substrate by mass spectrometry using Maldi. In one embodiment of the present invention, sample is prepared for Maldi using a solution dispense/layering method. In the solution dispense/layering method described herein, the bacterial suspension that will be dispensed is first evaluated to determine its turbidity as an indication of the concentration of bacteria in the suspension. One such standard method for the measure of turbidity is the McFarland turbidity standard. The McFarland turbidity standard is well known to those skilled in the art and not described in detail herein.

The bacterial suspension may be created using a method such as the method described WO2013147610 to Botma et al., entitled "Automated Selection of Microorganisms and Identification Using Maldi" and US Patent Publication 2012/0009558 to Armstrong et al. entitled "Method and Apparatus for Identification of Bacteria," the disclosures of which are hereby incorporated by reference in their entirety.

The solution dispense layering method requires, as implied by its name, the formation of two or more layers of solution for Maldi. A selected volume of sample is applied on the Maldi plate and dried. Subsequently, at least a second layer of sample is applied (preferably the same volume) as the first layer. The second layer is dried. Optionally, more layers can be deposited and dried. After the final of the two or more layers is dried, the sample is processed for Maldi (e.g. by adding formic acid and then applying the matrix over the sample as described herein). The sample is then evaluated by Maldi. The solution dispense/layer method has been determined to provide acceptable Maldi results for liquid samples with McFarland turbidity values significantly less than 2.0 for both Gram positive and Gram negative bacteria.

For example, in one embodiment, if the liquid bacterial suspension (prepared from a bacterial colony picked from an agar plate and suspended in water (mass spectrometry grade) as referenced above, has a value of 0.5 McFarland, that value is significantly below the value of 2.0 McFarland, which is an indication that the solution dispense/layering sample preparation should be used to prepare this sample for Maldi.

After determining to use solution dispense/layering to prepare the sample for Maldi, the amount of sample is selected per layer. In the above example with a sample having a 0.5 McFarland value, the volume per layer of at least about 3 µl but not exceeding about 4 µl is selected. The number of layers is governed by the turbidity value and the sample volume. Once the volume of the layer is selected and deposited on the Maldi plate, the sample is dried. The exact drying conditions are a matter of design choice and are selected to provide quick drying while preserving sample integrity for Maldi testing. Suitable drying conditions are readily determined by one skilled in the art. For example, the drying steps can be completed at either ambient temperature or with the assistance of a hot plate (illustratively, about 40° C. to about 45° C.). After drying, a second layer of sample is deposited over the first layer. The second layer has the same volume as the first layer. If needed, additional layers are added and dried. Since the layering method requires additional time and resources, the number of layers is limited to that number needed to obtain accurate results from Maldi.

Following the solution dispense/layering sample deposition, the sample target well is processed using the typical Maldi procedure (addition of 70% formic acid and matrix).

It has been determined that the sample preparation process for Maldi depends upon a variety of factors, but most significantly: i) the concentration of the microorganisms in the sample; ii) the volume of the sample; and iii) if applicable, the number of dispenses. The microbial concentration is reflected by the turbidity of the sample. Roughly, the higher the turbidity, the higher the microbial concentration. The method described herein begins with a sample turbidity measurement. Turbidity is measured by standard nephelometry using techniques and equipment well known to the skilled person. Nephelometry is not described in detail herein. Once the turbidity is assessed, a decision on how to go about sample preparation for Maldi is made. Such a determination is made by evaluating the turbidity information and sample volume. In those embodiments of the present invention where an automated evaluation and determination is contemplated, the sample information is entered into a data base. The data base (pre-programmed with information regarding the sample preparation best suited to the particular sample) outputs the recommended method for Maldi sample preparation.

In another embodiment, a system for evaluating a sample and determining the appropriate Maldi preparation protocol is contemplated. Preferably, the system is fully automated. In the automated embodiment of the system, a processor controls the Maldi preparation protocol, depending upon information that the processor receives regarding the sample. The sample is obtained either directly from a PBC or picked from a plated culture. In the automated systems, the sample is obtained using robotics. Robotic mechanisms that obtain biological samples for testing are well known to the skilled person and not described in detail herein. In other embodiments, the system is semi-automated. In the semi-automated embodiments, the sample is obtained manually.

After the sample is obtained, it is diluted. In the automated system, dilution is controlled by instructions from the processor. The system dilutes the sample to a predetermined volume (e.g., 4.5 ml) using sterile water as described above. Dilution can also be performed manually in the semi-automated embodiments.

Once the sample is diluted, the system measures sample turbidity. Preferably, the system deploys automated equipment to measure turbidity. Automated equipment for measuring sample turbidity is known to one skilled in the art and not described in detail herein. In the semi-automated embodiments, turbidity is measure manually.

The system processor compares the measured turbidity with a predetermined turbidity threshold. If the processor determines that the sample turbidity is within a predetermined range of turbidity values, then the processor provides instructions to transfer a predetermined volume of the diluted sample to the Maldi plate. The automated system prepares the sample for Maldi (i.e. the addition of formic acid to disrupt the cell wall of the microorganisms thereby releasing their proteins followed by application of Maldi matrix solution over the sample prior to Maldi as described elsewhere herein) based on instructions from the processor. In the semi-automated system, once instructions for the volume of sample to be deposited on the Maldi plate are received, the Maldi plate is prepared manually. If the processor determines that turbidity is above the predetermined range, the processor provides instructions to prepare a Maldi sample using less than the typical volume (i.e. if a 0.5 µl is normally deposited on the Maldi plate, only 0.25 µl is deposited on the Maldi plate instead for the high turbidity samples). If the processor determines that turbidity is below the predetermined range, the sample is deposited in layers on the Maldi plate, with drying of the sample between deposits. The deposition of multiple layers of the sample on a Maldi plate is described above. As noted above, in the fully automated embodiments, the system has automation that deposits the sample on the Maldi plate based on instructions from the processor. In the semi-automated embodiment, an operator deposits the sample on the Maldi plate based on instructions from the processor.

BRIEF DESCRIPTION OF THE DRAWINGS

FIG. 1 is an illustration of data used to formulate a statistical model used in one embodiment of the method described herein, including the parameters used and the values of the parameters used;

FIG. 2 illustrates additional conditions used to develop the statistical model described herein;

FIGS. 3A and 3B are lists of microorganisms that were used to test the method describe herein;

FIG. 5 describe the number of correct identifications (of the bacteria listed in FIG. 3) from Maldi (species identification) for different sample preparation parameters;

FIGS. 6A and 6B compares the Maldi score for 0.25 McFarland samples prepared with multiple dispenses with and without drying, for a variety of different microorganisms;

FIG. 7A-7C compares the Maldi score for 0.25 McFarland samples prepared with different sample volumes/number of dispenses, for a variety of different microorganisms;

DETAILED DESCRIPTION

Figure 4A:
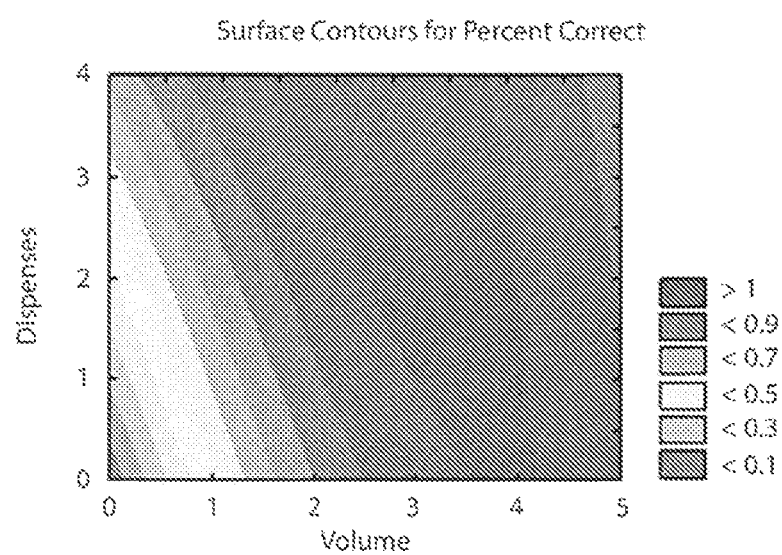
FIGS. 4A-4C are surface response plots from statistical models that illustrate what Maldi sample preparation parameters yield acceptable Maldi results.

The present invention contemplates methods for preparing samples for Maldi using a solution dispense/layering technique in which multiple layers of sample are dispensed on a Maldi plate. The dispensed sample is dried between dispenses. Such a method is illustrated herein to offer improvement in Maldi scores for a broad range of microorganisms.

One skilled in the art is aware that Maldi identification results are affected by the amount of cells deposited onto the Maldi plate. A standardized microbial suspension provides a uniform dispersion of cells, leading to more precise and reproducible results. In one embodiment, the microbial suspension is standardized prior to deposition onto the solid surface adapted to be placed in an apparatus configured to determine the identity of microorganisms by Maldi mass spectrometry. The microbial suspension can be optionally adjusted to a certain McFarland standard. Creation of the standardized microbial suspension can be accomplished by various methods well known to those skilled in the art, for example, using an inoculation loop, micro dropper, or other physical methods. In a preferred embodiment, a microbial suspension is adjusted to a McFarland standard of at least 0.25 prior to its inoculation onto a Maldi plate. The conditions for inoculation (i.e. dispense volume and number of dispenses) are selected to provide a sample likely to yield an acceptably high Maldi score, which is preferably at least about 2 or above.

In the described embodiments, samples for the microorganisms listed in FIG. 3 were prepared for Maldi. Several different methods that were used to prepare samples for Maldi are described below.

Method 1:

First, a 2.0 McFarland for each microorganism listed in FIG. 3A in a sterile diluent (e.g. BBL™ (Becton Dickinson)) was prepared. Three spots were formed on the MALDI target plate. Each spot was 1 µl in volume. The samples were then dried using a hot plate at about 40° C. to about 45° C. The MALDI target plate was obtained from Bruker. After the samples were dried, 1 µl of 70% formic acid was applied on the spot. The samples were again dried. Then 1 µl of α-cyano-hydroxy cinnanic acid (HCCA) matrix was placed over the spot and the sample was dried and analyzed on Bruker MALDI using instrument standard settings. MALDI successfully identified the genus and species of 28 out of 29 of the microorganisms listed in FIG. 3A.

Method 2:

First, a 1.0 McFarland for each microorganism listed in FIG. 3A was prepared using a sterile diluent to dilute the sample. Three spots were formed on the Maldi target plate. Each spot was 2 µl in volume. The samples were then dried using a hot plate at about 40° C. to about 45° C. The Maldi target plate was obtained from Bruker. After the samples were dried, 1 µl of 70% formic acid was applied on the spot. The samples were again dried. Then 1 µl of HCCA matrix was placed over the spot and the sample was dried and analyzed on Bruker Maldi using instrument standard settings. Maldi successfully identified the genus and species of 26 out of 29 of the microorganisms listed in FIG. 3A.

Method 3:

First a 1.0 McFarland for each microorganism listed in FIG. 3A was prepared using a sterile diluent. Three spots were formed on the Maldi target plate. Each spot was 1 µl in volume. The samples were then dried using a hot plate at about 40° C. to about 45° C. Another 1 µl was formed on each of the dried spots. Those spots were then dried. The Maldi target plate was obtained from Bruker. After the samples were dried, 1 µl of 70% formic acid was applied on the spot. The samples were again dried. Then 1 µl of HCCA matrix was placed over the spot and the sample was dried and analyzed on a Bruker Maldi using standard settings. Maldi successfully identified the genus and species of 29 out of 29 of the microorganisms listed in FIG. 3A.

Example 1

Samples with a 0.5 McFarland value were prepared and evaluated for the number of microorganisms correctly identified by Maldi. First 0.5 McFarland samples for each microorganism listed in FIG. 3A were prepared using a sterile diluent. The samples were formed on the Maldi plate according to the following Table 1:

TABLE 1

| McFarland | Dispense Volume | Number of Dispenses | Positive Identifications (out of a total of 29) |
|---|---|---|---|
| 0.5 | 1 µl | 1 | 7 of 29 |
| 0.5 | 1 µl | 2 (with drying between dispenses) | 28 of 29 |
| 0.5 | 1 µl | 3 (with drying between dispenses) | 29 of 29 |
| 0.5 | 1 µl | 4 (with drying between dispenses) | 29 of 29 |
| 2 | 1 µl | 1 | 28 of 29 |

Figure 1:
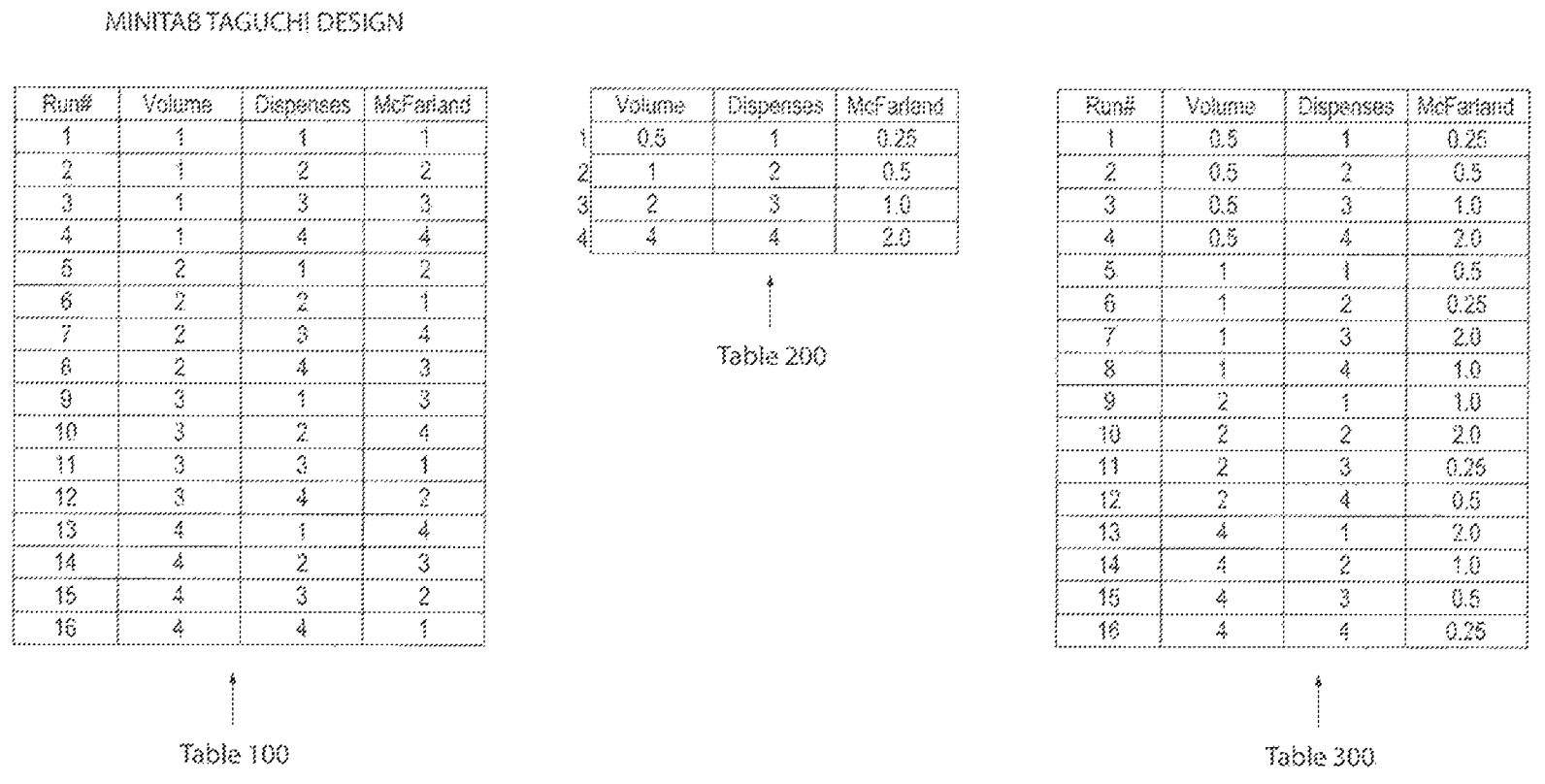

To create the statistical model, four values for each of the three parameters were selected. The four values and the parameters associated with those values are set forth in Table 200 in FIG. 1. These values were then loaded into Minitab 16 utilizing the Design of Experiment (DOE) Taguchi Design (which is commercially available, well known to one skilled in the art and not described in detail herein). This initial design created a series of 16 experimental runs using the parameter matrix as set forth in Table 100 of FIG. 1. Table 100 enumerates the integer associated with the parameters in Table 200. Table 300 enumerates the actual parameters for each run. The runs were conducted on the fifteen (15) most difficult bacteria to detect, using Maldi identification from the challenge set in FIG. 3B (a more challenging array of microorganisms to detect than those enumerated in FIG. 3A). Data was compiled and analyzed using Statistica version 12 (commercially available software well known to one skilled in the art). All three parameters, McFarland, dispense volumes and number of dispenses were significant to a determination of whether or not a sample had an acceptable chance to yield a correct Maldi score.

Figure 4B:
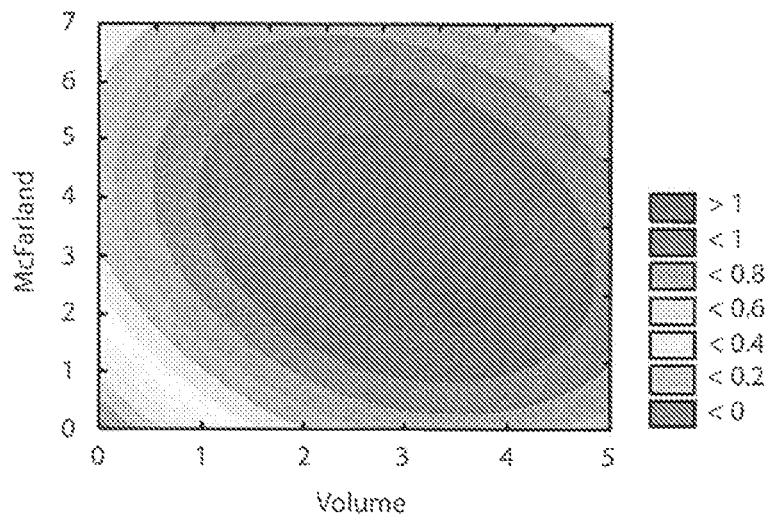
Figure 4C:
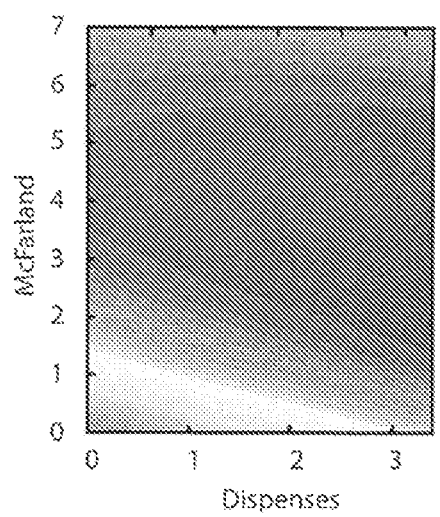

Surface response plots were created and the interactions studied. These surface response plots illustrate that acceptable Maldi results will vary depending upon the values for McFarland, number of dispenses and volume. The plots illustrate that a higher McFarland is not always the key to a desirable Maldi score (2.0 or higher for genus and species confirmation). For example a 2.0 McFarland and a lower McFarland (e.g. 0.5), could give the same correct Maldi result with a higher dispense volume (FIG. 4B) and/or a greater number of dispense/dry cycles (FIG. 4C) to the target plate. Table 500 sets forth additional sample parameters for Maldi sample preparation that were used to supplement the model. These samples had significantly higher McFarland values (~5.0) to determine the upper limit interactions.

Maldi values for the samples were obtained using a Bruker MALDI Biotyper LT. All samples were prepared using the above protocols. Values for McFarland, dispense volume and number of dispenses are as set forth in FIGS. 1 and 2. The runs 1-22 set forth in FIG. 5 were performed for each microorganism enumerated in FIG. 3B. When sample depositions were complete, the sample was dried and set with 1 µl of 70 percent aqueous Formic Acid. The sample was again dried and sealed with 1 µl Bruker HCCA Matrix.

To prepare samples to obtain the desired McFarland value the sample was diluted with 5 ml of sterile sample diluent. The desired McFarland values were achieved using a BD Phoenix™ Spec Nephelometer and BD Phoenix™ Spec Calibration Kit Methods.

As set forth in FIG. 1, Table 200, the samples were prepared using the following values:
i) McFarland values: 0.25, 0.5, 1.0, 2.0;
ii) Sample volume: 0.5 µl, 1.0 µl, 2.0 µl, 4.0 µl; and
iii) Number of dispenses: 1, 2, 3, and 4.

When sample depositions were complete, the sample was dried and set with 1 µl of 70 percent aqueous Formic Acid. The sample was again dried and sealed with 1 µl Bruker HCCA Matrix. Matrix solutions were prepared using 50% Acetonitrile, 47.5% Water & 2.5% TFA. The solvent was obtained from Sigma Aldrich.

Since three spots were prepared on each plate for each microorganism, three Maldi scores were obtained for each microorganism. So for the 22 runs enumerated in Tables 300 and 500 (FIGS. 1 and 2), 66 Maldi scores were obtained for each microorganism.

As can be seen from FIG. 5, the highest percentages of correct Maldi scores (a correct result was a Maldi score of 2.0 or above) were obtained for a variety of different parameters. Generally, for a lower McFarland value sample, the volume and number of dispenses is required to be higher to get a higher percentage of correct Maldi scores. For example, for a 0.25 McFarland sample, a dispense volume of 4 µl and 4 dispenses with drying between dispenses was required to achieve 84% correct Maldi scores.

Example 2

Samples (0.25 McFarland) were prepared and spiked with the microorganisms enumerated in FIG. 3B. Samples were prepared using the procedure described generally above. Three spots were formed on the Maldi target plate. Each spot was 1 µl in volume. The samples were then dried on a hot plate at 40° C. to 45° C. Two target plates were prepared for each sample. The Maldi target plate was obtained from Bruker. On the first plate, the deposited sample was dried, after which another 1 µl spot of sample was placed on the dried first spot. On the second plate the first spot was not dried before the second spot was deposited thereon. After the spots were completely deposited, the spots on both plates were dried. Then, 1 µl of 70% formic acid was applied on the dried spots on both plates. The samples were again dried. Then 1 µl of HCCA matrix was placed over the spot and the sample was dried and analyzed on Bruker Maldi. Maldi successfully identified 39 out of 45 spots of spiked samples (at the genus level) for those samples prepared using a drying step between depositing spots on the Maldi plate. Maldi successfully identified 29 out of 45 spots of spiked samples (at the species level) for those samples prepared using a drying step between depositing spots on the Maldi plate. Since samples were spiked with one of 15 microorganisms and there were three spots for each spiked sample, a total of 45 sample spots were evaluated by Maldi.

Maldi successfully identified 39 out of 45 spots of spiked samples (at the genus level) for those samples prepared without a drying step between depositing spots on the Maldi plate. However, Maldi-TOF successfully identified only 24 out of 45 spots of spiked samples (at the species level) for those samples prepared without a drying step between depositing spots on the Maldi plate. A summary of these results is set forth in Table 2 below. Results are reported as the best of the three, rather than the aggregate of positives. From this it can be seen that one more microorganism was detected with a drying step between deposits than without a drying step.

TABLE 2

| | 0.25 McFarland | |
|---|---|---|
| | 1 µl/1 µl (Drying) | 1 µl/1 µl (No Drying) |
| Genus and Species ID | 29 | 24 |
| Genus ID only | 10 | 15 |

TABLE 2-continued

| | 0.25 McFarland | |
|---|---|---|
| | 1 µl/1 µl (Drying) | 1 µl/1 µl (No Drying) |
| No ID | 6 | 6 |
| Correct ID | 13/15 | 12/15 |

The Maldi scores for each microorganism evaluated are listed in FIG. 6. Note that Maldi scores below 1.7 were considered "no identification." Maldi scores between 1.7 but below 2 were considered positive identifications at the genus level but not the species level. Maldi scores at or above 2 were considered positive identifications at both genus and species levels. For the samples that were dried between first and second dispenses, the percent of positive identifications at the genus and species levels was 64%, compared with 53% of such identifications when the sample was not dried between the dispenses. This indicates that the solution dispense/layering (w/drying) method described herein provides a marked advantage over multiple dispenses with no drying therebetween for the test of "low McFarland" samples using Maldi-TOF.

Example 3

Figure 7A:
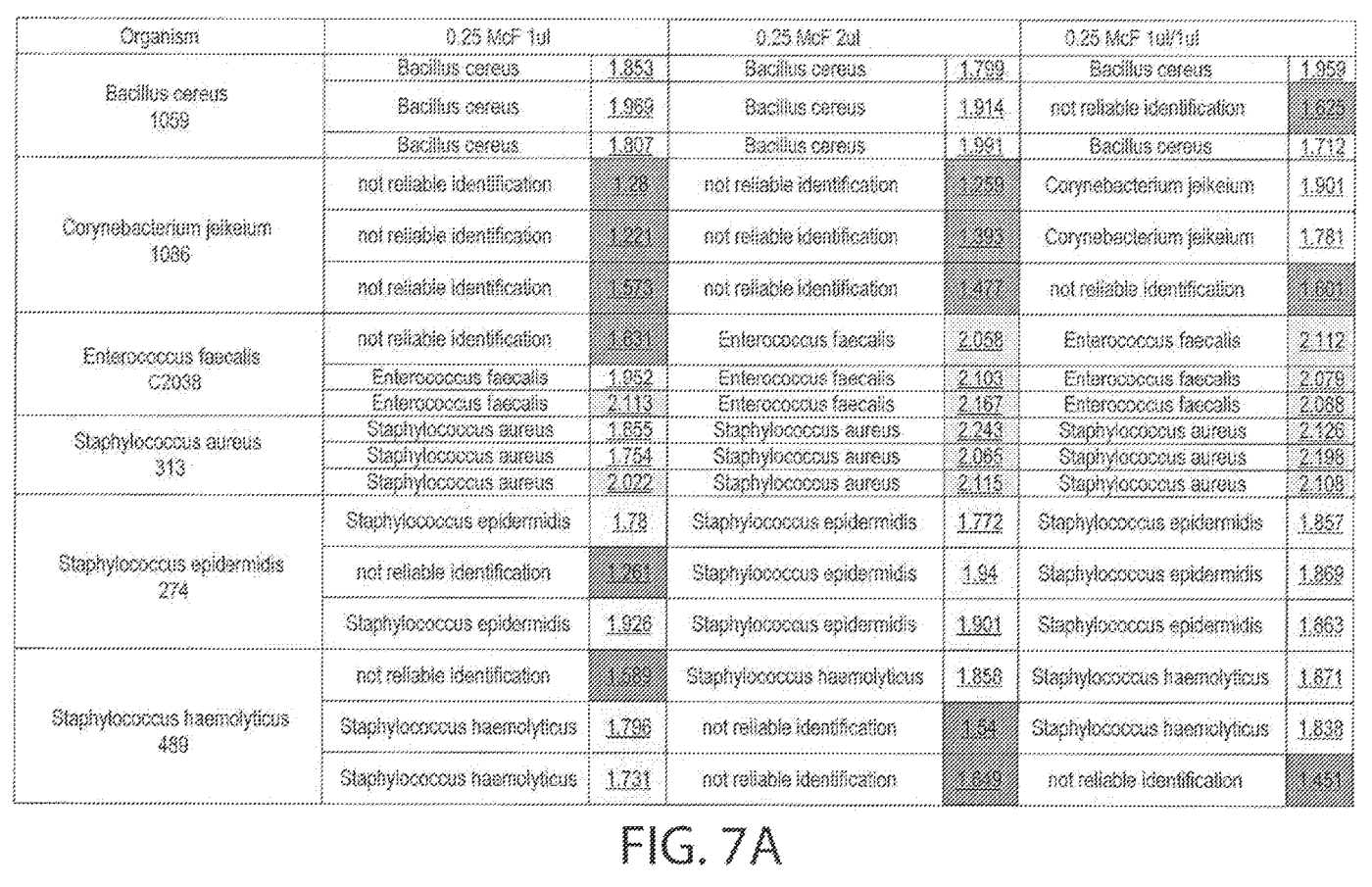

Samples (0.25 McFarland) were prepared and spiked with the microorganisms enumerated in FIG. 3B. Samples were prepared using the procedure described generally above. Three spots were formed on each Maldi target plate. Three target plates were prepared for each sample. The Maldi target plates were obtained from Bruker. On the first plate, three spots of 1 µl sample each were dispensed. On the second plate, three spots of 2 µl sample each were dispensed. On the third plate, three spots of 1 µl sample each were dispensed, dried, and another 1 µl sample spot was formed on each dried spot. After the spots were completely deposited, the spots on the plates were dried. Then, 1 µl of 70% formic acid was applied on the dried spots on both plates. The samples were again dried. Then 1 µl of HCCA matrix was placed over the spot and the sample was dried and analyzed on Bruker Maldi. Maldi successfully identified 31 out of 42 spots of spiked samples (at the genus level) for those samples prepared with a single 1 µl dispense of 0.25 McFarland sample. Maldi successfully identified 33 out of 42 spots of spiked samples (at the genus level) for those samples prepared with a single 2 µl dispense of 0.25 McFarland sample. Maldi successfully identified 36 out of 42 spots of spiked samples (at the genus level) for those samples prepared with a 1 µl dispense of 0.25 McFarland sample followed by drying and a second 1 µl dispense. These results are reported in Table 3 below and in FIG. 7. When results are reported as a "best of three, it is clear that the best result (correct IDs for the greatest number of different microorganisms) was obtained using 0.25 McFarland with 1 µl/1 µl by layering.

TABLE 3

| | Maldi EVALUATION | | |
|---|---|---|---|
| | 0.25 McFarland 1 µl Addition | 0.25 McFarland 2 µl Addition | 0.25 McFarland 1 µl/1 µl (Layering) |
| Genus and Species ID | 10 | 18 | 24 |
| Genus ID only | 21 | 15 | 12 |
| No ID | 11 | 9 | 6 |
| Correct ID | 6/14 | 8/14 | 9/14 |
| % CORRECT | 24% | 43% | 57% |

At the species level, the solution dispense/layering method using two 1 µl dispenses with an intervening drying step provided 24 correct identifications at the species level (compared with 18 for a 2 µl single dispense and 10 for a 1 µl single dispense). This data again shows that the solution dispense/layering method provides markedly more accurate Maldi scores than single dispenses for samples having lower McFarland values.

In one embodiment, the microorganism from pure isolates or a PBC sample is identified by: i) obtaining the sample suspected to contain at least one microorganism from growth media (i.e. either from PBC or from a sub-culture on an agar plate); ii) determining the inoculation parameters of the sample, those parameters including, for the determined McFarland value of the inoculate, the dispense volume and the number of dispenses; iii) depositing at least a portion of the sample on a solid surface adapted to be placed in an apparatus configured to determine the identity of microorganisms by Maldi mass spectrometry using the prescribed dispense volume and number of dispenses); iv) treating the sample with at least one reagent; such reagents including a volatile acid, an organic solvent, and/or a combination of organic solvent and a volatile acid; v) placing a Maldi matrix solution over the treated sample; and vi) identifying the microorganism by mass spectrometry. In one embodiment the volatile acid is at least 70% formic acid. In another embodiment the volatile acid is at least 80% formic acid. In another embodiment the volatile acid is at least 90% formic acid. Unless otherwise specified herein, the formic acid solutions are aqueous solutions. In another embodiment the volatile acid is at least 100% formic acid (e.g. neat). In another embodiment, the sample is treated with at least 70% formic acid in an organic solvent such as acetonitrile, methanol, ethanol, acetone, or ethyl acetate prior to placing a Maldi matrix solution over the sample. In another embodiment, the sample is treated with at least 80% formic acid in an organic solvent such as acetonitrile, methanol, ethanol, acetone, or ethyl acetate prior to placing a Maldi matrix solution over the sample. In another embodiment, the sample is treated with at least 90% formic acid in an organic solvent such as acetonitrile, methanol, ethanol, acetone, or ethyl acetate prior to placing a Maldi matrix solution over the sample. In one embodiment, the sample deposited on the solid surface is allowed to dry prior to adding the volatile acid, to prevent the sample from diluting the volatile acid. In another embodiment, the volatile acid is dried prior to placing the Maldi matrix solution over the sample. Examples of the volatile acids that may be used in the various embodiments of the invention include, but are not limited to, formic acid, acetic acid, trifluoracetic acid and hydrochloric acid.

After the sample is dried on the Maldi plate and combined with the volatile acid alone or in combination with an organic solvent, the combination of sample and reagents is dried. Drying is defined as allowing the liquid to evaporate sufficiently so as not to dilute any liquid subsequently added. While the sample can be dried in ambient air, a heating source, such as a heating block, hot plate, heating oven or infrared heating lamp can be used to accelerate the evaporation of the liquid portion of the combined sample and reagents. These drying methods do not change the spectrum of the sample upon identification by Maldi.

After drying, the Maldi matrix is applied over the sample treated with reagent(s). Any Maldi matrix solution known to those skilled in the art can be used in the disclosed methods. These matrix solutions include, but are not limited to, α-cyano-4-hydroxycinnamic acid (HCCA), 2,5-dihydroxybenzoic acid (DHB), 3,5-dimethoxy-4-hydroxycinnamic acid (SPA), 3-hydroxypicolinic acid (HPA), 3,4-dihydroxycinnamic acid, 2-(4-hydroxyphenylazo)-benzoic acid, 2-amino-4-methyl-5-nitropyridine, and 2,4,6-trihydroxy acetophenone (THAP).

In an alternative embodiment, the microorganism is identified by: i) preparing a microbial suspension of a sample suspected of containing at least one microorganism; ii) determining the turbidity of the microbial suspension; iii) selecting the volume and number of dispenses to be used to deposit, from a microbial suspension, at least a portion of the sample on a solid surface adapted to be placed in an apparatus configured to determine the identity of microorganisms by Maldi mass spectrometry; iv) depositing the sample on the Maldi plate using the selected parameters; v) optionally, fixing the microorganism with an organic solvent, e.g. ethanol, a fixative, e.g. formaldehyde, or by applying heat, generally up to about 37° C. (i.e. approximately body temperature); vi) covering the sample with at least 70% formic acid; v) drying the sample; vi) placing a Maldi matrix solution over the treated sample; vii) drying the sample; and viii) identifying the microorganism by mass spectrometry. Fixatives such as formaldehyde are well known to one skilled in the art and are not described in detail herein.

Figure 8:
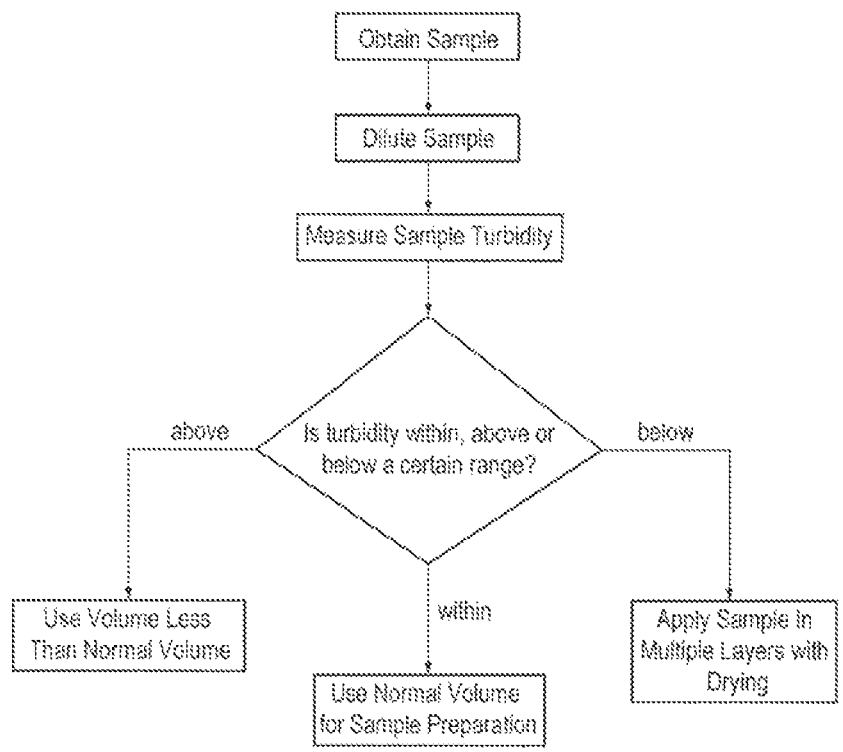
FIG. 8 is a flow chart for the embodiment of the present invention where sample preparation is based upon measured sample turbidity.

Referring to FIG. 8, on example of the present invention contemplates obtaining a biological sample. The sample is combined with a diluent suited to deliver the sample to a Maldi plate. The turbidity of the sample/diluent mixture is measured. If the measured turbidity is within a predetermined range, an aliquot with a predetermined volume is deposited on the Maldi plate. If the measured turbidity is higher than a predetermined range, then a smaller volume of sample is deposited on the Maldi plate. If the measured turbidity is less than the predetermined range, then the above-described sample preparation protocol using multiple dispenses with drying between dispenses is used.

In one exemplary embodiment, a sample is obtained and a suspension is prepared. The turbidity is measured. If the turbidity (in McFarland) is between about 2 and about 6, about 3 μl is deposited on the Maldi plate. If the sample turbidity is higher than about 6, then the amount of sample deposited on the Maldi plate is reduced to about 1 μl. If the sample turbidity is less than about 2 but in the range of about 1 to about 2, then about 3 μl of sample is deposited on the Maldi plate, dried, and a second 3 μl sample is deposited and dried. If the sample turbidity is about 0.5 to about 1, then three "layers" of sample, each about 3 μl, are deposited and dried. If the sample turbidity is about 0.25 to about 0.5, then 4 "layers" of sample (3 μl each) are deposited and dried.

After the sample is deposited and dried, the samples are processed for Maldi as described herein.

An automated system for preparing a biological sample for evaluation by Matrix-Assisted Laser Desorption Ionization Time of Flight mass spectrometry is also contemplated. Such system has a programmable controller (e.g. a processor) in communication with a sample preparation device. The programmable controller communicates instructions to the sample preparation device to pick a colony from a plated culture. An example of such a device is the InoqulA™ which is obtained commercially from BD Kiestra™. The processor provides instructions to add an amount of diluent or sample processing reagents, as appropriate, to the sample to provide a sample solution having a predetermined volume. Automated systems that dilute samples to a predetermined volume are well known to the skilled person and not described in detail herein. After sample dilution, the turbidity of the sample is measured. Turbidity is measured by a variety of techniques including absorbance, transmittance and manual methods. Embodiments of the system contemplate the use of a nephelometer to measure turbidity.

As used herein, "nephelometer" is an instrument that is capable of measuring the amount of solid particles in a suspension. As used herein, "nephelometry" refers to a method by which the amount of suspended solids in a suspension can be measured. Nephelometers are well known to the skilled person and not described in detail herein.

The processor is in communication with the instrument that measures sample turbidity. The processor has a memory that stores a value or range of value for an acceptable turbidity. The processor compares the measure value with stored values. If the sample concentration is within the predetermined range, the processor provides instruction to apply a first predetermined volume of sample to a substrate adapted to deliver a sample to a device configured to perform mass spectrometry as described above.

If the processor determines that a measured sample concentration is higher than the predetermined range, the processor provides instructions to apply a second predetermined volume of sample to the substrate adapted to deliver the sample to the device configured to perform mass spectrometry. The second predetermined volume is less than the first predetermined volume.

If the processor determines that a measured sample concentration is lower than the predetermined range the processor provides instructions to: i) apply a third predetermined volume of the sample to a substrate adapted to deliver the sample to the device configured to perform mass spectrometry; ii) dry the sample; iii) apply a second application of the third predetermined volume of the sample over the dried sample on the substrate; and iv) dry the sample according to the methods described herein.

Thereafter, the processor instructs the system to apply a matrix over the deposited sample, the matrix being adapted for use in the mass spectrometer. The system also has a transport mechanism for placing the prepared sample in a mass spectrometry device for testing.

Figure 9:
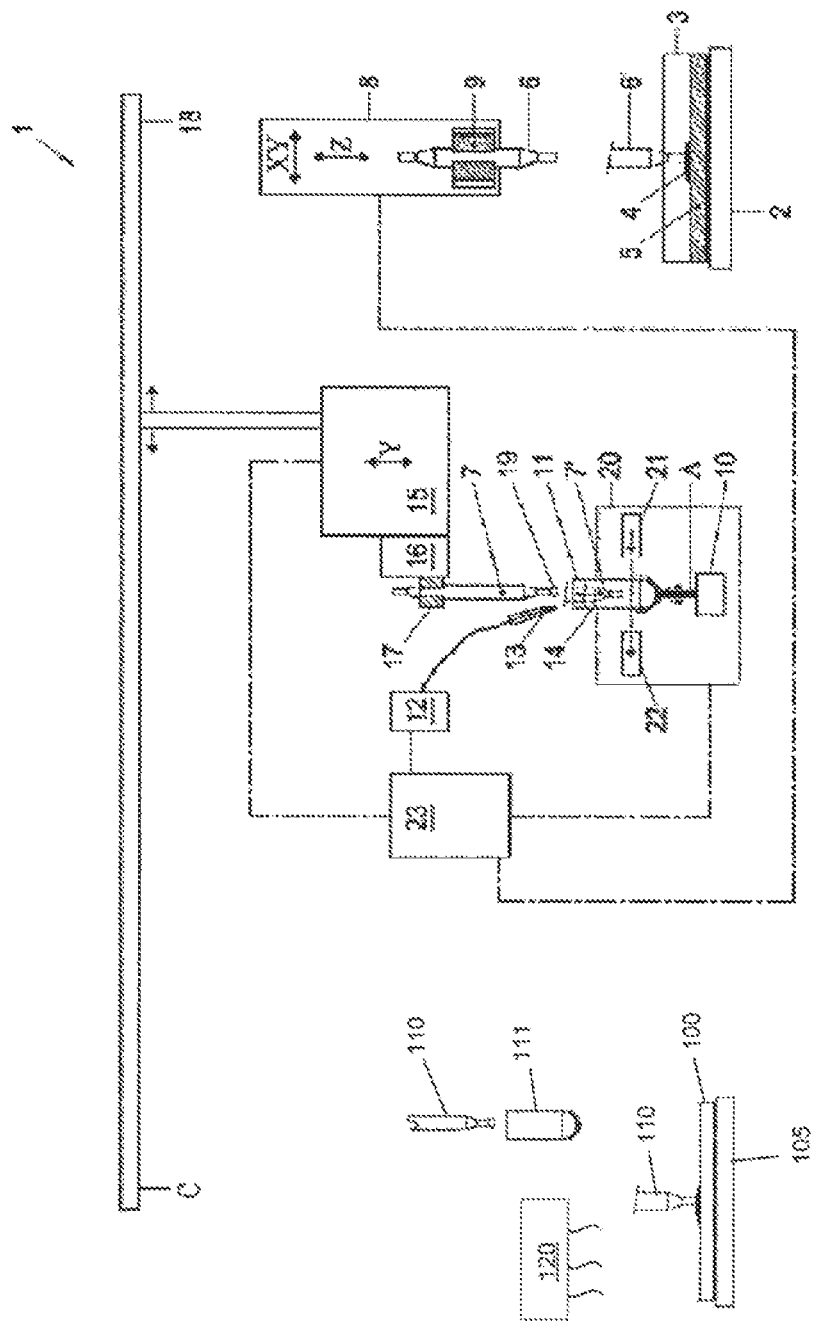
FIG. 9 is a schematic of a system used to practice the method described herein.

FIG. 9 schematically shows an embodiment of a system 1 for the automatic preparation of a suspension of a sample of a microorganism according to the invention. Said system 1 comprises a stage 2 for a culture dish 3 comprising a microorganism 4 on a nutritional layer 5, such as a layer of agar gel.

The system 1 has a first picking tool 6 and a further picking tool 7. A positioning device 8 comprises a picking tool holder 9 for, in the shown embodiment releasably holding a picking tool, in the embodiment shown in FIG. 1 the picking tool holder 9 holds the first picking tool 6. The positioning device 8 is arranged for positioning the first picking tool 6 in a starting position (shown in solid lines in FIG. 9) above the culture dish 3 and is arranged for automatically lowering and raising the first picking tool 6 towards and away from the culture dish 3, such that the first picking tool 6 can be positioned in a position (indicated with broken lines 6') in which it contacts the microorganism 4 and picks up a sample of the microorganism. After the first picking tool 6 has picked up a sample, the positioning device 8 raises and positions the first picking tool 6 in a transfer position. In the embodiment shown in FIG. 9 the transfer position is identical to the starting position. In other embodiments the starting and transfer positions may be different from each other.

The system 1 according to the invention further comprises a suspension tube holder 10 for holding a suspension tube 11 which can contain a suspension medium which is dispensed from an automatic suspension medium dispenser 12, which in the shown embodiment has a dispensing nozzle 13 for automatically dispensing a suspension medium 14 in the suspension tube 11 held in the suspension tube holder 10. In the present embodiment the suspension tube holder 10 is a rotatable suspension tube holder for rotating the suspension tube 11 around a vertical axis A.

A transferring device 15 is incorporated in the system 1 for automatically transferring a picking tool from the transfer position of the positioning device 8 to a position above the suspension tube 11 held in the suspension tube holder 10. In the embodiment shown, the transferring device 15 comprises a transfer holder 16 with a grasping tool 17 for releasably holding a picking tool. The transferring device 15 is illustrated as deploying a transfer track 18, such as a rail, for linear movement thereon as indicated by the arrows. However, other deck mounted transfer mechanisms are contemplated. In this manner the transferring device 15 may be moved to the positioning device 8, such that the grasping tool 17 can take over the picking tool from the positioning device 8. The picking tool holder 9 thereafter releases the picking tool after the grasping means 17 has grasped the picking tool. In the embodiment shown in FIG. 9 the second or further picking tool 7 having previously picked up a sample 19 of the microorganism 4 is positioned above the suspension tube 11 by the transferring device 15 in a starting position indicated by solid lines. The transferring device 15 is arranged for lowering the second picking tool 7 into the suspension medium 14 contained in the suspension tube 11, in which position the second picking tool 7' with the sample 19 is submerged in the suspension medium 14 as indicated by broken lines in FIG. 9. Thereafter the transferring device 15 positions the second picking tool 7 in a waiting position above the suspension tube 11, which waiting position is in the embodiment shown in FIG. 9 identical to the starting position. In other embodiments the waiting position and the starting position may be different from each other.

The system further is provided with a turbidity meter 20 for performing measurements of the turbidity of the suspension medium 14 contained in the suspension tube 11 held in the suspension tube holder 10. As generally known in the art a turbidity meter can provide measurement values which are a measure of the concentration of material, in the present case the concentration of a microorganism suspended in the suspension medium. In the embodiment shown in FIG. 9 the turbidity meter 20 comprises a laser 21 which transmits laser light towards and through the suspension medium and a sensor 22 which detects the amount of laser light transmitted through the suspension medium. In addition there is a further sensor (not indicated in the drawing) which is e.g. arranged perpendicular to the path of the laser light to detect the amount of laser light which has been scattered by the suspension.

The operation of the inventive device is controlled by a controller 23, for example comprising a microprocessor, which is communicatively connected (as indicated by the signal lines) to the positioning device 8, the transferring device 15, the automatic suspension medium dispenser 12, and the turbidity meter 20 for automatically controlling the movement of the positioning device 8, the movement of the transferring device 15, the operation of the automatic suspension medium dispenser 12 and the operation of the turbidity meter 20, respectively. In addition the controller 23 might be directly communicatively connected to other parts of the system 1 such as, for example, the pick tool holder 9, the transfer holder 16, the laser 21 and the sensor 22.

In the embodiment shown in FIG. 9 the controller 23 is arranged for controlling the turbidity meter 20 such that the turbidity measurement of the suspension medium 14 is started before the second picking tool 7 is submerged in the suspension medium 14. In addition, the controller 23 controls the rotatable suspension tube holder 10 for starting the rotation of the suspension tube 11 held in the holder 10 before the second picking tool 7 is submerged in the suspension medium 14, and for maintaining the rotation of the suspension tube 11 during the measurement of the turbidity of the suspension medium 14. In this manner the turbidity meter 20 provides an on-line measurement value to the controller 23 which value is indicative of the measured turbidity, and thus the concentration of the microorganism.

The controller 23 comprises a memory, in which a first and a second threshold value are stored, in which the first threshold value is equal to or greater than the second threshold value. If the turbidity measurement value provided by the turbidity meter is equal to or between the first and second threshold value, the concentration/amount of microorganism in the suspension medium is sufficient to allow the suspension tube with the suspension to be further processed. In that case the controller 23 provides a signal that the suspension tube can be processed further. In addition in this situation the second picking tool 7 can be discarded e.g. by transferring the transferring device to a position C in which the grasping means 17 are activated to release the second picking tool 7.

In case the final measurement value of the turbidity meter is above the first threshold value previously stored in a memory of the controller 23 then the concentration of the microorganism is too high to allow the suspension tube to be processed further. In that situation the controller 23 controls the automatic suspension medium dispenser 12 to supply an additional amount of suspension medium into the suspension tube 11. This additional amount of suspension medium is based on the initial amount of suspension medium, the final measurement value and the value of the first and/or second threshold value such that the addition of the additional amount of suspension medium to the suspension medium already present in the suspension tube 11 will lead to a concentration of microorganism in the suspension medium which satisfies the requirement for further processing, as can be confirmed by an additional or further measurement of the turbidity by the turbidity meter 20.

In case the final measurement value of the turbidity meter 20 is below the second threshold value, meaning that the concentration of microorganism in the suspension medium is too low, the controller 23 controls the system 1 such that an additional sample of microorganism is picked up by the first picking tool 6 (alternatively the second or another picking tool can be used for picking up an additional sample). In yet other embodiments (described hereinbelow), multiple dispenses of suspension can be deposited in the same spot if the turbidity of the suspension is below specification. Thus, the controller 23 in this case controls the positioning of the transfer device 15 such that the second picking tool 7 is discarded as described above. Then (or simultaneously) the first picking tool 6 in the picking tool holder 9 of the positioning device 8 is lowered from the starting position above the culture dish 3 towards the culture dish and into contact with the microorganism 4 to pick up an additional sample of the microorganism. Thereafter, the first picking tool 6 is automatically raised with the additional sample of the microorganism away from the culture dish to the transfer position. Then the transferring device automatically transfers the first picking tool with the additional sample of the microorganism from the transfer position of the positioning device 8 to a position above the suspension tube 11. The first picking tool 6 with the additional sample of the microorganism is lowered into the suspension medium 14 and releases the additional sample of the microorganism in the suspension medium. Again the turbidity is measured, and the measured value is compared with the first and second threshold value stored in the memory of the controller 23. In this case the controller 23 can be arranged for controlling the movement of the transferring device 15 such that the first picking tool 6 is raised to the waiting position if the on-line measurement value of the turbidity performed by the turbidity meter 20 is equal to or lower than the first threshold value and equal to or greater than the second threshold value.

Suspension tubes, or alternately, vials or cuvettes which are particularly useful in the inventive system have a cross-section with a target maximum dimension of about 2 to about 12 mm, preferably about 3 mm. In these relatively small suspension tubes the controller 23 can control the automatic suspension medium dispenser 12 such that the supplied initial amount of suspension medium is about 0.1-5 ml, preferably less than about 1 ml.

After the suspension is prepared, aliquots of the suspension are automatically pipetted from the suspension tube 11 and deposited onto the Maldi plate 100. Maldi plate 100 is schematically illustrated as resting on support 105. This step is performed at a Maldi plate preparation station identified as location C that is apart from the location where the suspension is prepared. In certain embodiments the suspension tube 11 is moved to the location near the Maldi plate for Maldi plate preparation as described above. In other embodiments, an aliquot of suspension is removed from suspension tube 11 and that aliquot is used for Maldi plate preparation. The robotic pipettor is illustrated schematically as 110 in FIG. 9. Robotic pipettors are well known and not described in detail herein. The Maldi plate 100 is connected to a drying apparatus illustrated as heater 120.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method for preparing a biological sample for evaluation by Matrix-Assisted Laser Desorption Ionization Time of Flight mass spectrometry the method comprising:
    picking a biological sample from a colony of a microorganism disposed on a culture plate;
    diluting the biological sample to form a diluted sample;
    measuring a turbidity of the diluted sample;
    applying a first aliquot of the diluted sample to a surface adapted to deliver a sample to a device configured to perform mass spectrometry;
    drying the first aliquot of the diluted sample;
    applying a second aliquot of the sample over the first, dried aliquot;
    drying the second aliquot of the diluted sample;
    applying a matrix over the dried first and second aliquots of diluted sample, the matrix adapted for use in the mass spectrometer; and
    performing mass spectrometry on the sample;
    wherein, if the measured turbidity of the diluted sample is about 1 to about 2 McFarland, the first aliquot is about 3 µl and the second aliquot is about 3 µl;
    wherein, if the measured turbidity of the diluted sample is about 0.5 to less than about 1 McFarland, the first aliquot of the diluted sample is about 3 µl, the second aliquot of the diluted sample is about 3 and wherein the method further comprises applying a third aliquot of about 3 µl of the diluted sample over the dried first and second aliquots of the diluted sample and drying the third aliquot of the diluted sample, prior to the application of the matrix; and
    wherein if the measure turbidity of the diluted sample is about 0.25 to less than about 0.5 McFarland, the first aliquot of the diluted sample is about 3 µl, the second aliquot of the diluted sample is about 3 µl, and wherein the method further comprises applying a third aliquot of about 3 µl of the diluted sample over the dried first and second aliquots of the diluted sample, drying the third aliquot of the diluted sample, applying a fourth aliquot of about 3 µl of the diluted sample over the dried first, second and third aliquots of the diluted sample, and drying the fourth aliquot of diluted sample, prior to the application of the matrix.

2. The method of claim 1 wherein the sample is diluted by combining the sample with a sterile diluent.

3. The method of claim 1 wherein the biological sample is a portion of a colony of a microorganism picked from a culture plate.

4. The method of claim 1 wherein the surface is a plate adapted for use in a mass spectrometer.

5. The method of claim 1 wherein the matrix solution is selected from the group consisting of α-cyano-4-hydroxycinnamic acid (HCCA), 2,5-dihydroxybenzoic acid (DHB), 3,5-dimethoxy-4-hydroxycinnamic acid (SPA), 3-hydroxypicolinic acid (HPA), 3.4-dihydroxycinnamic acid, 2-(4-hydroxyphenylazo)-benzoic acid, 2-amino-4-methyl-5-nitropyridine, and 2,4,6-trihydroxy acetophenone (THAP).

6. The method of claim 1 wherein the drying is at a temperature of about room temperature to about 45° C.

7. The method of claim 1 wherein after applying the diluted sample, the diluted sample is treated with a reagent comprising at least one of a volatile acid, an organic solvent and combinations thereof.

8. The method of claim 7 wherein the volatile acid is at least 70% formic acid.

9. The method of claim 8 wherein the formic acid is combined with an organic solvent and the organic solvent is selected from the group consisting of acetonitrile, methanol, ethanol, acetone, or ethyl acetate.

* * * * *